United States Patent [19]

Seko et al.

[11] Patent Number: 5,756,769
[45] Date of Patent: May 26, 1998

[54] METHOD FOR PRODUCING PROPARGYLAMINE COMPOUNDS

[75] Inventors: Shinzo Seko, Toyonaka; Akihiko Nakamura, Takatsuki; Motoo Hazama, Toyonaka, all of Japan

[73] Assignee: Sumitomo Chemical Company, Ltd., Osaka, Japan

[21] Appl. No.: 866,126

[22] Filed: May 30, 1997

[30] Foreign Application Priority Data

May 31, 1996 [JP] Japan ............................. 8-138520
Dec. 20, 1996 [JP] Japan ............................. 8-341991

[51] Int. Cl.$^6$ .............. C07C 709/62; C07C 249/02; C07C 211/23
[52] U.S. Cl. .................. 549/74; 544/242; 544/336; 546/176; 546/526; 549/49; 549/467; 549/491; 564/375; 564/378; 564/383; 564/473; 564/509
[58] Field of Search ........................... 564/375, 378, 564/383, 473, 509; 549/74

[56] References Cited

U.S. PATENT DOCUMENTS

| | | | |
|---|---|---|---|
| 3,268,524 | 8/1966 | Moore et al. | 544/78 |
| 3,914,312 | 10/1975 | Castalgne | 564/470 |
| 4,743,617 | 5/1988 | Bargar et al. | 514/438 |
| 5,210,303 | 5/1993 | Sugiyama | 564/407 |

FOREIGN PATENT DOCUMENTS

| | | |
|---|---|---|
| 0281018 | 9/1988 | European Pat. Off. |
| 2600706 | 7/1976 | Germany |

OTHER PUBLICATIONS

K. Nakanishi (1955) *Nippon Kagaku Zasshi by Kikumasa Sato* 76, 1404–1406.
Marszak-Fleury (1957) *Bull. Soc. Chim.Fr.*, 490–493.
Glacet et al. (1963) *Bull. Soc. Chim.Fr.*, 2464–2467.
Lattrell et al. (1974) *Liebigs Ann.Chem.*, 870–900.
Koziara et al. (1985) *Synthesis*, 202–204.
Chauvelier et al. (1951) *Academie des Sciences*, 167–169.

*Primary Examiner*—Richard L. Raymond
*Attorney, Agent, or Firm*—Birch, Stewart, Kolasch & Birch, L.L.P.

[57] ABSTRACT

A method for producing a propargylamine compound represented by the general formula (I):

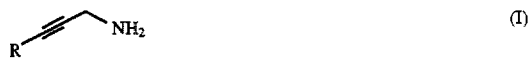

which comprises reacting a propargyl compound represented by the general formula (II):

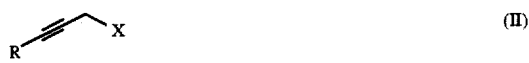

with an aromatic aldehyde represented by the general formula (III):

ArCHO     (III)

and ammonia to obtain an imine compound represented by the general formula (IV):

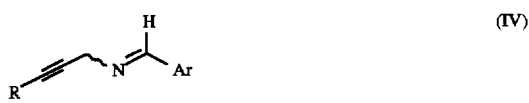

and hydrolyzing the resultant imine compound. It is to provide a method for producing a propargylamine compound from a propargyl compound by a simple operation without using a special facility, using ammonia as a reaction reagent, without producing a dipropatygylamine compound and a tripropargylamine compound as by-products.

8 Claims, No Drawings

METHOD FOR PRODUCING PROPARGYLAMINE COMPOUNDS

The present invention relates to a method for producing propargylamine compounds. Propargylamine compounds are useful as intermediates of drugs or pesticides and also have utility such as described in U.S. Pat. Nos. 4,743,617 and 3,914,312.

As the method for producing propargylamine compounds, a method of aminating propargyl compounds is known. Examples thereof include method of using hexamethylenetetramine as an aminating agent [Delepine reaction, Nippon Kagaku Zasshi, 76, 1404 (1955), Bull. Soc. Chim. Fr. 490 (1958)], method of using potassium phthalimide [Gabriel reaction, Bull. Soc. Chim. Fr. 2464 (1963), Justus Liebigs Ann. Chem., 870 (1974), Japanese Patent Kokai (Laid-Open) No. Sho-50-46609], method for using propargyl azide obtained from propargyl halide [Staudinger reaction, Synthesis, 202 (1985)] and the like.

However, regarding the method according to the Delepine reaction, the operation is complicated and it is difficult to separate a large amount of ammonium chloride produced as by-products after the completion of the reaction. Regarding the method according to the Gabriel reaction, the cost of potassium phthalimide is high and severe reaction conditions are required. The method according to the Staudinger reaction requires special production facilities for handling propargyl azide having high explosion properties. Therefore, all methods were not industrially satisfactory.

Although a method for producing propargylamine compounds, comprising reacting ammonia known as a cheap aminating agent with propargyl compounds is also known [Compt. Rend. 232, 167 (1951)], a large amount of dipropargylamine compounds and tripropargylamine compounds are produced as by-products according to this method and, therefore, the yield of the desired propargylamine compounds was considerably low.

Thus, the present inventors have intensively studied so as to develop a method for producing propargylamine compounds from propargyl compounds by a simple operation using a cheap reaction reagent, without using a special facility, without producing dipropargylamine compounds or tripropargylamine compounds as by-products. As a result, it has been found that propargylamine compounds can be produced in an industrially advantageous manner by reacting propargyl compounds with aromatic aldehydes and ammonia to selectively obtain imine compounds, and hydrolyzing the imine compounds, thereby accomplishing the present invention.

That is, the present invention provides a method for producing a propargylamine compound represented by the general formula (I):

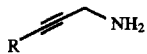
(I)

[wherein R represents a hydrogen atom, a lower alkyl group, an aryl group or a heteroaryl group], which comprises reacting a propargyl compound represented by the general formula (II):

(II)

[wherein R has the same meanings as defined above; and X represents a halogen atom or a sulfonyloxy group] with an aromatic aldehyde represented by the general formula (III):

 (III)

[wherein Ar represents an aryl group] and ammonia to obtain an imine compound represented by the general formula (IV):

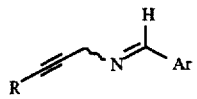
(IV)

[wherein R and Ar have the same meanings as defined above], and hydrolyzing the resultant imine compound.

In the propargyl compound represented by the general formula (II), examples of the lower alkyl group for substituent R include straight-chain or branched alkyl groups having 1 to 6 carbon atoms, such as methyl group, ethyl group, n-propyl group, isopropyl group, n-butyl group, isobutyl group, sec-butyl group, t-butyl group, n-pentyl group, neopentyl group, n-hexyl group and the like.

Examples of the aryl group include phenyl group, naphthyl group and the like. These aryl groups may be substituted with 1 to 3 substituents selected from halogen atom, nitro group, lower alkyl group and lower alkoxy group. Examples of the halogen atom include fluorine atom, chlorine atom, bromine atom and iodine atom. Examples of the lower alkyl group include straight-chain or branched alkyl groups having 1 to 6 carbon atoms, such as methyl group, ethyl group, n-propyl group, isopropyl group, n-butyl group, isobutyl group, sec-butyl group, t-butyl group, n-pentyl group, neopentyl group, n-hexyl group and the like. Examples of the lower alkoxy group include straight-chain or branched alkoxy groups having 1 to 6 carbon atoms, such as methoxy group, ethoxy group, n-propoxy group, isopropoxy group, n-butoxy group, isobutoxy group, sec-butoxy group, t-butoxy group, n-pentyloxy group, neopentyloxy group, n-hexyloxy group and the like.

Examples of the heteroaryl group include the aryl groups having 1, to 3 heteroatoms selected from nitrogen sulfur and oxygen atom, such as 2-thienyl group, 3-thienyl group, 2-furyl group, 3-furyl group, 2-pyridyl group, 2-quinolyl group, 3-pyrazyl group, 5-pyrimidinyl group, 2-benzo[b]thienyl group, 3-benzo[b]thienyl group, 2-benzo[b]furanyl group, 3-benzo[b]furanyl group and the like. These heteroaryl groups may be substituted with 1 or 2 substituents selected from halogen atom, lower alkyl group and lower alkoxy group. Examples of the halogen atom include fluorine atom, chlorine atom, bromine atom and iodine atom. Examples of the lower alkyl group include straight-chain or branched alkyl groups having 1 to 6 carbon atoms, such as methyl group, ethyl group, n-propyl group, isopropyl group, n-butyl group, isobutyl group, sec-butyl group, t-butyl group, n-pentyl group, neopentyl group, n-hexyl group and the like. Examples of the lower alkoxy group include straight-chain or branched alkoxy groups having 1 to 6 carbon atoms, such as methoxy group, ethoxy group, n-propoxy group, isopropoxy group, n-butoxy group, isobutoxy group, sec-butoxy group, t-butoxy group, n-pentyloxy group, neopentyloxy group, n-hexyloxy group and the like.

Examples of the halogen atom for substituent X include chlorine atom, bromine atom and iodine aton. Examples of the sulfonyloxy group for substituent X include a lower alkylsulfonyloxy group and an arylsulfonyloxy group. The lower alkylsulfonyloxy group is exemplified by the alkylsulfonyloxy groups having 1 to 6 carbon atoms such as methanesulfonyloxy group, ethanesulfonyloxy group, 1-propanesulfonyloxy group, 2-propanesulfonyloxy group, 1-butanesulfonyloxy group, 2-butanesulfonyloxy group, 2-methylpropane-1-sulfonyloxy group, 2-methylpropane-2-sulfonyloxy group, 1-pentanesulfonyloxy group, 2,2- dimethylpropane-1-sulfonyloxy group, 1-hexanesulfonyloxy group and the like. These lower alkylsulfonyloxy group may be substituted by 1 to 5 halogen atoms such as fluorine and chlorine atom. The arylsulfonyloxy group is exemplified by benzenesulfonyloxy group and naphthalenesulfonyloxy group and these arylsulfonyloxy group may be substituted by 1 to 3 substituents such as halogen atom, nitro group, lower alkyl group and lower alkoxy group. The halogen atom of the substituents is fluorine atom, chlorine atom, bromine atom or iodine atom and the lower alkyl group of the substituents is exemplified by the straight chain or branched alkyl groups having 1 to 6 carbon atoms such as methyl group, ethyl group, n-propyl group, isopropyl group, n-butyl group, isobutyl group, sec-butyl group, t-butyl group, n-pentyl group, neopentyl group, n-hexyl group and the like. The lower alkoxy group of the substituents is exemplified by the straight chain or branched alkoxy groups having 1 to 6 carbon atoms such as methoxy group, ethoxy group, n-propoxy group, isopropoxy group, n-butoxy isobutoxy group, sec-butoxy group, t-butoxy group, n-pentyloxy group, neopentyloxy group, n-hexyloxy group and the like.

Typical examples of the sulfonyloxy group for substituent X include methanesulfonyloxy group, ethanesulfonyloxy group, 1-propanesulfonyloxy group, 2-propanesulfonyloxy group, 1-butanesulfonyloxy group, trifluoromethanesulfonyloxy group benzenesulfonyloxy group, p-toluenesulfonyloxy group and the like.

Examples of the propargyl compound include propargyl chloride, propargyl bromide, propargyl iodide, propargyl methanesulfonate, propargyl benzenesulfonate, propargyl p-toluenesulfonate, propargyl trifluoromethanesulfonate, 2-butynyl bromide, 2-butynyl methanesulfonate, 2-butynyl benzenesulfonate, 2-butynyl p-toluenesulfonate, 2-butynyl trifluoromethanesulfonate, 2-pentynyl methanesulfonate, 4-methyl-2-pentynyl methanesulfonate, 2-hexynyl bromide, 4-methyl-2-hexynyl benzenesulfonate, 5-methyl-2-hexynyl methanesulfonate, 2-heptynyl p-toluenesulfonate, 5-methyl-2-heptynyl methanesulfonate, 2-octynyl bromide, 2-nonynyl methanesulfonate, 3-phenyl-2-propynyl methanesulfonate, 3-phenyl-2-propynyl benzenesulfonate, 3-phenyl-2-propynyl p-toluenesulfonate, 3-(4-fluorophenyl)-2-propynyl methanesulfonate, 3-(3-chlorophenyl)-2-propynyl methanesulfonate, 3-(2-bromophenyl)-2-propynyl benzenesulfonate, 3-(4-nitrophenyl)-2-propynyl methanesulfonate, 3-(4-methylphenyl)-2-propynyl p-toluenesulfonate, 3-(4-methoxyphenyl)-2-propynyl methanesulfonate, 3-(2,4-dimethylphenyl-2-propynyl trifluoromethanesulfonate, 3-(2,4,5-trimethylphenyl)-2-propynyl methanesulfonate, 3-(1-naphthyl)-2-propynyl p-toluenesulfonate, 3-(2-naphthyl)-2-propynyl benzenesulfonate, 3-(2-thienyl)-2-propynyl methanesulfonate, 3-(5-fluoro-2-thienyl)-2-propynyl methanesulfonate, 3-(5-chloro-2-thienyl)-2-propynyl methanesulfonate, 3-(5-bromo-2-thienyl)-2-propynyl methanesulfonate, 3-(5-methyl-2-thienyl)-2-propynyl methanesulfonate, 3-(3-thienyl)-2-propynyl benzenesulfonate, 3-(5-fluoro-3-thienyl)-2-propynyl p-toluenesulfonate, 3-(5-chloro-3-thienyl)-2-propynyl trifluoromethanesulfonate, 3-(5-bromo-3-thienyl)-2-propynyl methanesulfonate, 3-(5-methyl-3-thienyl)-2-propynyl benzenesulfonate, 3-(2-furyl)-2-propynyl methanesulfonate, 3-(5-fluoro-2-furyl)-2-propynyl methanesulfonate, 3-(5-chloro-2-furyl)-2-propynyl methanesulfonate, 3-(5-bromo-2-furyl)-2-propynyl methanesulfonate, 3-(5-methyl-2-furyl)-2-propynyl methanesulfonate, 3-(3-furyl)-2-propynyl benzenesulfonate, 3-(5-fluoro-3-furyl)-2-propynyl p-toluenesulfonate, 3-(5-chloro-3-furyl)-2-propynyl trifluoromethanesulfonate, 3-(5-bromo-3-furyl)-2-propynyl methanesulfonate, 3-(5-methyl-3-furyl)-2-propynyl benzenesulfonate and the like.

All of these propargyl compounds can be easily produced from the corresponding alcohols (cf. JP-2524513).

In the aromatic aldehyde represented by the general formula (III), examples of the aryl group for substituent Ar include phenyl group, naphthyl group and the like. These aryl groups may be substituted with 1 to 3 substituents selected from halogen atom, nitro group, lower alkyl group and lower alkoxy group. Examples of the halogen atom include fluorine atom, chlorine atom, bromine atom and iodine atom. Examples of the lower alkyl group include straight-chain or branched alkyl groups having 1 to 6 carbon atoms, such as methyl group, ethyl group, n-propyl group, isopropyl group, n-butyl group, isobutyl group, sec-butyl group, t-butyl group, n-pentyl group, neopentyl group, n-hexyl group and the like. Examples of the lower alkoxy group include straight-chain or branched alkoxy groups having 1 to 6 carbon atoms, such as methoxy group, ethoxy group, n-propoxy group, isopropoxy group, n-butoxy group, isobutoxy group, sec-butoxy group, t-butoxy group, n-pentyloxy group, neopentyloxy group, n-hexyloxy group and the like.

Examples of the aromatic aldehyde include benzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2,4-dichlorobenzaldehyde, 2-bromobenzaldehyde, 3-bromobenzaldehyde 4-bromobenzaldehyde, 4-iodobenzaldehyde, 3-nitrobenzaldehyde, 4-nitrobenzaldehyde, 2-methylbenzaldehyde, 3-methylbenzaldehyde, 4-methylbenzaldehyde, 2,4-dimethylbenzaldehyde, 4-ethylbenzaldehyde, 4-butylbenzaldehyde, 2-methoxybenzaldehyde, 3-methoxybenzaldehyde, 4-methoxybenzaldehyde, 3,4-dimethoxybenzaldehyde, 3,4-methylenedioxybenzaldehyde, 1-naphthalenecarboaldehyde, 2-naphthalenecarboaldehyde and the like. An amount of the aromatic aldehyde used is normally within the range from 0.7 to 10 mol, preferably from 0.8 to 5 mol, to 1 mol of the propargyl compound.

Ammonia may be an aqueous ammonia solution or an ammonia gas. Aqueous ammonia solution is preferably used because it can be supplied into the reaction system without using a blowing device and a post-treatment is simple. When using aqueous ammonia solution, a concentration thereof is normally from 5 to 30% by weight. An amount of ammonia used is normally within the range from 2 to 20 mol, preferably from 3 to 15 mol, to 1 mol of the propargyl compound.

The reaction is normally conducted in a solvent. It is preferred that the solvent is hydrophobic because good yield is obtained and the treatment after the completion of the reaction can be simplified. Examples of the hydrophobic solvent include aromatic hydrocarbon such as benzene, toluene, xylene, and the like; aliphatic hydrocarbon such as hexane, cyclohexane, heptane, and the like; halogenated hydrocarbon such as chlorobenzene, dichlorobenzene, chloroform, 1,2-dichloroethane, and the like; and ether compound such as diethyl ether, diisopropyl ether, t-butyl methyl ether, diethoxymethane, and the like. These solvents may be used alone or in combination thereof. An amount of the solvent used is normally within the range from 0.5 to 50 parts by weight, preferably from 1 to 30 parts by weight, to 1 part by weight of the propargyl compound.

The reaction is conducted, for example, by mixing the propargyl compound with the aromatic aldehyde in the solvent, and supplying ammonia. When using the aqueous ammonia solution as ammonia, the propargyl compound may be supplied after mixing the aromatic aldehyde with ammonia in the solvent. The reaction temperature is normally within the range from 0° to 100° C., preferably from 15° to 50° C.

Thus, the imine compound represented by the general formula (IV) is obtained. Examples of the imine compound include N-benzylidene-2-propynylamine, N-(2-fluorobenzylidene)-2-propynylamine, N-(3-fluorobenzylidene)-2-propynylamine, N-(4-fluorobenzylidene)-2-propynylamine, N-(2-chlorobenzylidene)-2-propynylamine, N-(3-chlorobenzylidene)-2-propynylamine, N-(4-chlorobenzylidene)-2-propynylamine, N-(2,4-dichlorobenzylidene)-2-propynylamine, N-(2-bromobenzylidene)-2-propynylamine, N-(3-bromobenzylidene)-2-propynylamine, N-(4-bromobenzylidene)-2-propynylamine, N-(4-iodobenzylidene)-2-propynylamine, N-(3-nitrobenzylidene)-2-propynylamine, N-(4-nitrobenzylidene)-2-propynylamine, N-(2-methylbenzylidene)-2-propynylamine, N-(3-methylbenzylidene)-2-propynylamine, N-(4-methylbenzylidene)-2-propynylamine, N-(2,4-dimethylbenzylidene)-2-propynylamine, N-(4-ethylbenzylidene)-2-propynylamine, N-(4-butylbenzylidene)-2-propynylamine, N-(2-methoxybenzylidene)-2-propynylamine, N-(3-methoxybenzylidene)-2-propynylamine, N-(4-methoxybenzylidene)-2-propynylamine, N-(3,4-dimethoxybenzylidene)-2-propynylamine, N-(3,4-methylenedioxybenzylidene)-2-propynylamine, N-(2-propynyl)-1-naphthylmethanimine, N-(2-propynyl)-2-naphthylmethanimine, N-benzylidene-2-butynylamine, N-(2-chlorobenzylidene)-2-butynylamine, N-(3-chlorobenzylidene)-2-butynylamine, N-(4-chlorobenzylidene)-2-butynylamine, N-(2,4-dichlorobenzylidene)-2-butynylamine, N-(3-nitrobenzylidene)-2-butynylamine, N-(4-nitrobenzylidene)-2-butynylamine, N-(2-methylbenzylidene)-2-butynylamine, N-(3-methylbenzylidene)-2-butynylamine, N-(4-methylbenzylidene)-2-butynylamine, N-(2-methoxybenzylidene)-2-N-(3-methoxybenzylidene)-2-butynylamine, N-(4-methoxybenzylidene)-2-butynylamine N-(3,4-methylenedioxybenzylidene)-2-butynylamine, N-benzylidene-2-pentynylamine, N-(2-chlorobenzylidene)-2-pentynylamine, N-(3-chlorobenzylidene)-2-pentynylamine, N-(4-chlorobenzylidene)-2-pentynylamine, N-(2,4-dichlorobenzylidene)-2-pentynylamine, N-(3-nitrobenzylidene)-2-pentynylamine, N-(4-nitrobenzylidene)-2-pentynylamine, N-benzylidene-4-methyl-2-pentynylamine, N-(2-chlorobenzylidene)-4-methyl-2-pentynylamine, 4-methyl-N-(4-nitrobenzylidene)-2-pentynylamine, N-benzylidene-2-hexynylamine, N-(2-chlorobenzylidene)-2-hexynylamine, N-(3-chlorobenzylidene)-2-hexynylamine, N-(4-chlorobenzylidene)-2-hexynylamine, N-(2,4-dichlorobenzylidene)-2-hexynylamine, N-(3-nitrobenzylidene)-2-hexynylamine, N-(4-nitrobenzylidene)-2-hexynylamine, N-benzylidene-4-methyl-2-hexynylamine, N-(2-chlorobenzylidene)-4-methyl-2-hexynylamine, 4-methyl-N-(4-nitrobenzylidene)-2-hexynylamine, N-benzylidene-5-methyl-2-hexynylamine, N-(2-chlorobenzylidene)-5-methyl-2-hexynylamine, 5-methyl-N-(4-nitrobenzylidene)-2-hexynylamine, N-benzylidene-2-heptynylamine, N-(2-chlorobenzylidene)-2-heptynylamine, N-(3-chlorobenzylidene)-2-heptynylamine, N-(4-chlorobenzylidene)-2-heptynylamine, N-(2,4-dichlorobenzylidene)-2-heptynylamine, N-(3-nitrobenzylidene)-2-heptynylamine, N-(4-nitrobenzylidene)-2-heptynylamine, N-benzylidene-5-methyl-2-heptynylamine, N-(2-chlorobenzylidene)-5-methyl-2-heptynylamine, 5-methyl-N-(4-nitrobenzylidene)-2-heptynylamine, N-benzylidene-2-octynylamine, N-(2-chlorobenzylidene)-2-octynylamine, N-(3-chlorobenzylidene)-2-octynylamine, N-(4-chlorobenzylidene)-2-octynylamine, N-(2,4-dichlorobenzylidene)-2-octynylamine, N-(3-nitrobenzylidene)-2-octynylamine, N-(4-nitrobenzylidene)-2-octynylamine, N-benzylidene-2-nonynylamine, N-(2-chlorobenzylidene)-2-nonynylamine, N-(3-chlorobenzylidene)-2-nonynylamine, N-(4-chlorobenzylidene)-2-nonynylamine, N-(2,4-dichlorobenzylidene)-2-nonynylamine, N-(3-nitrobenzylidene)-2-nonynylamine, N-(4-nitrobenzylidene)-2-nonynylamine, N-benzylidene-3-phenyl-2-propynylamine, N-(2-chlorobenzylidene)-3-phenyl-2-propynylamine, N-(3-chlorobenzylidene)-3-phenyl-2-propynylamine, N-(4-chlorobenzylidene)-3-phenyl-2-propynylamine, N-(2,4-dichlorobenzylidene)-3-phenyl-2-propynylamine, N-(3-nitrobenzylidene)-3-phenyl-2-propynylamine, N-(4-nitrobenzylidene)-3-phenyl-2-propynylamine, N-benzylidene-3-(3-chlorophenyl)-2-propynylamine, N-(2-chlorobenzylidene)-3-(3-chlorophenyl)-2-propynylamine, N-(3-chlorobenzylidene)-3-(3-chlorophenyl)-2-propynylamine, N-(4-chlorobenzylidene)-3-(3-chlorophenyl)-2-propynylamine, 3-(3-chlorophenyl)-N-(2,4-dichlorobenzylidene)-2-propynylamine, 3-(3-chlorophenyl)-N-(3-nitrobenzylidene)-2-propynylamine, 3-(3-chlorophenyl)-N-(4-nitrobenzylidene)-2-propynylamine, N-benzylidene-3-(2-bromophenyl)-2-propynylamine, 3-(2-bromophenyl)-N-(2-chlorobenzylidene)-2-propynylamine, 3-(2-bromophenyl)-N-(3-chlorobenzylidene)-2-propynylamine, 3-(2-bromophenyl)-N-(4-chlorobenzylidene)-2-propynylamine, 3-(2-bromophenyl)-N-(2,4-dichlorobenzylidene)-2-propynylamine, 3-(2-bromophenyl)-N-(3-nitrobenzylidene)-2-propynylamine, 3-(2-bromophenyl)-N-(4-nitrobenzylidene)-2-propynylamine, N-benzylidene-3-(4-nitrophenyl)-2-propynylamine, N-(2-chlorobenzylidene)-3-(4-nitrophenyl)-2-propynylamine, N-(3-chlorobenzylidene)-3-(4-nitrophenyl)-2-propynylamine, N-(4-chlorobenzylidene)-3-(4-nitrophenyl)-2-propynylamine, N-(2,4-dichlorobenzylidene)-3-(4-nitrophenyl)-2-propynylamine, N-(3-nitrobenzylidene)-3-(4-nitrophenyl)-2-propynylamine, N-(4-nitrobenzylidene)-3-(4-nitrophenyl)-2-propynylamine, N-benzylidene)-3-(4-methylphenyl)-2-propynylamine, N-(2-chlorobenzylidene)-3-(4-methylphenyl)-2-propynylamine, N-(3-chlorobenzylidene)-3-(4-methylphenyl)-2-propynylamine, N-(4-chlorobenzylidene)-3-(4-methylphenyl)-2-propynylamine, N-(2,4-dichlorobenzylidene)-3-(4-methylphenyl)-2-propynylamine, 3-(4-methylphenyl)-N-(3-nitrobenzylidene)-2-propynylamine, 3-(4-methylphenyl)-N-(4-nitrobenzylidene)-2-propynylamine, N-benzylidene-3-(4-methoxyphenyl)-2-propynylamine, N-(2-chlorobenzylidene)-3-(4-methoxyphenyl)-2-propynylamine, N-(3-chlorobenzylidene)-3-(4-methoxyphenyl)-2-propynylamine, N-(4-chlorobenzylidene)-3-(4-methoxyphenyl)-2-propynylamine, N-(2,4-dichlorobenzylidene)-3-(4-methoxyphenyl)-2-propynylamine, 3-(4-methoxyphenyl-N-(3-nitrobenzylidene)-2-propynylamine, 3-(4-methoxyphenyl)-N-(3-nitrobenzylidene)-2-propynylamine, 3-(4-methoxyphenyl)-N-(4-nitrobenzyliden-2-propynylamine, N-benzylidene-3-(2,4-dimethylphenyl)-2-propynylamine, N-(2-chlorobenzylidene)-3-(2,4-dimethylphenyl)-2-propynylamine, N-(3-chlorobenzylidene)-3-(2,4-dimethylphenyl)-2-propynylamine, N-(4-chlorobenzylidene)-3-(2,4-dimethylphenyl)-2-propynylamine, N-(2,4-dichlorobenzylidene)-3-(2,4-dimethylphenyl)-2-propynylamine, 3-(2,4-dimethylphenyl)-N-(3-nitrobenzylidene)-2-propynylamine, 3-(2,4-dimethylphenyl)-N-(4-nitrobenzylidene)-2-propynylamine, N-benzylidene-3-(2,4,5-trimethylphenyl)-2-propynylamine, N-(2-chlorobenzylidene)-3-(2,4,5-trimethylphenyl)-2-propynylamine, N-(3-chlorobenzylidene)-3-(2,4,5-trimethylphenyl)-2-propynylamine, N-(4-chlorobenzylidene)-3-(2,4,5-trimethylphenyl)-2-propynylamine, N-(2,4-dichlorobenzylidene)-3-(2,4,5-trimethylphenyl)-2-propynylamine, N-(3-nitrobenzylidene)-3-(2,4,5-trimethylphenyl)-2-propynylamine, N-(4-nitrobenzylidene)-3-(2,4,5-trimethylphenyl)-2-propynylamine, N-benzylidene-3-(1-naphthyl)-2-propynylamine, N-(2-chlorobenzylidene)-3-(1-naphthyl)-2-propynylamine, N-(3-chlorobenzylidene)-3-(1-naphthyl)-2-propynylamine, N-(4-chlorobenzylidene)-3-(1-naphthyl)-2-propynylamine, N-(2,4-dichlorobenzylidene)-3-(1-naphthyl)-2-propynylamine, 3-(1-naphthyl)-N-(3-nitrobenzylidene)-2-propynylamine, 3-(1-naphthyl)-N-(4-nitrobenzylidene)-2-propynylamine, N-benzylidene-3-(2-naphthyl)-2-propynylamine, N-(2-chlorobenzylidene)-3-(2-naphthyl)-2-propynylamine, N-(3-chlorobenzylidene)-3-(2-naphthyl)-2-propynylamine, N-(4-chlorobenzylidene)-3-(2-naphthyl)-2-propynylamine, N-(2,4-dichlorobenzylidene)-3-(2-naphthyl)-2-propynylamine, 3-(2-naphthyl)-N-(3-nitrobenzylidene)-2-propynylamine, 3-(2-naphthyl)-N-(4-nitrobenzylidene)-2-propynylamine, N-benzylidene-3-(2-thienyl)-2-propynylamine, N-benzylidene-3-(5-fluoro-2-thienyl)-2-propynylamine, N-benzylidene-3-(5-chloro-2-thienyl)-2-propynylamine, N-benzylidene-3-(5-bromo-2-thienyl)-2-propynylamine, 3-(5-bromo-2-thienyl)-N-(2-chlorobenzylidene)-2-propynylamine, 3-(5-bromo-2-thienyl)-N-(4-chlorobenzylidene)-2-propynylamine, 3-(5-bromo-2-thienyl)-N-(4-nitrobenzylidene)-2-propynylamine, N-benzylidene-3-(5-methyl-2-thienyl)-2-propynylamine, N-benzylidene-3-(3-thienyl)-2-propynylamine, N-benzylidene-3-(5-fluoro-3-thienyl)-2-propynylamine, N-benzylidene-3-(5-chloro-3-thienyl)-2-propynylamine, N-benzylidene-3-(5-bromo-3-thienyl)-2-propynylamine, N-benzylidene-3-(5-methyl-3-thienyl)-2-propynylamine, N-benzylidene-3-(2-furyl)-2-propynylamine, N-benzylidene-3-(5-fluoro-2-furyl)-2-propynylamine, N-benzylidene-3-(5-chloro-2-furyl)-2-propynylamine, N-benzylidene-3-(5-bromo-2-furyl)-2-propynylamine, N-benzylidene-3-(5-methyl-3-furyl)-2-propynylamine, N-benzylidene-3-(3-furyl)-2-propynylamine, N-benzylidene-3-(5-fluoro-3-furyl)-2-propynylamine, N-benzylidene-3-(5-chloro-3-furyl)-2-propynylamine, N-benzylidene-3-(5-bromo-3-furyl)-2-propynylamine, N-benzylidene-3-(5-methyl-3-furyl)-2-propynylamine and the like.

The imine compound thus obtained may be used for the following hydrolysis after separating from the reaction mixture as a solution thereof, or used after isolation from the solution.

In order to separate the imine compound from the reaction mixture as the solution thereof, the organic phase may be obtained from the reaction mixture by layer separation after the completion of the reaction. The imine compound can be easily isolated from the solution, for example, by a ordinary method of distilling off the solvent. The imine compound may be further purified by a method such as distillation, column chromatography and the like.

Then, the resulting imine compound is hydrolyzed to obtain the desired propargylamine compound.

In case of hydrolysis, an acid is normally used. Examples of the acid include inorganic acid such as hydrochloric acid, surfuric acid, hydrobromic acid and the like; and organic acid such as p-toluenesulfonic acid, benzenesulfonic acid, methanesulfonic acid and the like. An amount of the acid used is normally within the range from 0.45 to 5 mol, preferably from 0.9 to 2.5 mol, to 1 mol of the imine compound. An amount of water used is normally within the range of not less than 0.8 mole to 1 mole of the imine compound. An amount of water used is preferably not more than 50 parts by weight, more preferably not more than 20 parts by weight to 1 part by weight of the imine compound.

In case of hydrolysis, a solvent is ordinary used. Examples of the solvent include aromatic hydrocarbon such as benzene, toluene, xylene and the like; aliphatic hydrocarbon such as hexane, cyclohexane, heptane and the like; halogenated hydrocarbon such as chlorobenzene, dichlorobenzene, chloroform, 1,2-dichloroethane and the like; ketones such as methyl ethyl ketone, methyl isobutyl ketone and the like; alcohols such as methanol, ethanol, 2-propanol and the like; and ethers such as diethyl ether, diisopropyl ether and the like. These solvent may be used alone or in combination thereof. An amount of the solvent used is normally within the range from 0.8 to 50 parts by weight, preferably from 1.5 to 30 parts by weight, to 1 part by weight of the imine compound.

The hydrolysis is, for example, conducted by adding an acid and water after mixing the imine compound with the solvent. When using an organic phase obtained by phase separation as a solution of the imine compound, the acid and water may be added to the solution. The hydrolysis temperature is normally within the range from 0° to 100° C., preferably from 15° to 80° C.

Thus, the desired propargylamine compound is formed. When using the hydrophobic solvent in the above-mentioned hydrolysis, the propargylamine compound can be easily isolated from an aqueous phase after partitioning the reaction mixture into the aqueous phase and organic phase.

In the separation procedure, when the amount of the solvent or water used in the above-mentioned hydrolysis is small, the separation organic phase from aqueous one can not be easily conducted, sometimes. In that case, the separation may be conducted, after adding the hydrophobic solvent or water appropriately. Examples of the hydrophobic solvent include aromatic hydrocarbon such as benzene, toluene, xylene and the like; aliphatic hydrocarbon such as hexane, cyclohexane, heptane and the like; halogenated hydrocarbon such as chlorobenzene, dichlorobenzene, chloroform, 1,2-dichloroethane and the like; ketones such as methyl ethyl ketone, methyl isobutyl ketone and the like; and ethers such as diethyl ether, diisopropyl ether and the like.

It is preferred to conduct phase separation by normally heating the reaction mixture to not more than 100° C., preferably not more than 80° C., in view of operation properties.

In order to isolate the propargylamine compound from the aqueous phase after phase separation, for example, it may be extracted after adding a base to the resulting aqueous phase.

Examples of the base include inorganic base such as sodium hydroxide, potassium hydroxide, sodium carbonate, potassium carbonate and the like. An amount of the base used is normally from 0.4 to 20 mol, preferably from 0.9 to 10 mol, to 1 mol of the acid used for the above-mentioned hydrolysis. The base may be added in the form of the solid as it is, or added as an aqueous solution. When using the base as the aqueous solution, the concentration of the base in the solution is normally from 3 to 80% by weight, preferably from 10 to 50% by weight.

Examples of the solvent used for extraction include aromatic hydrocarbon such as benzene, toluene, xylene and the like; aliphatic hydrocarbon such as hexane, cyclohexane, heptane and the like; halogenated hydrocarbon such as chlorobenzene, dichlorobenzene, chloroform, 1,2-dichloroethane and the like; ketones such as methyl ethyl ketone, methyl isobutyl ketone and the like; and ethers such as diethyl ether, diisopropyl ether, t-butyl methyl ether and the like. These solvent may be used alone or in combination thereof. An amount of the solvent used is normally within the range from 0.2 to 50 parts by weight, preferably from 0.5 to 20 parts by weight, to 1 part by weight of the aqueous phase.

The desired propargylamine compound can be easily obtained from the organic phase after extracting, for example, by a normal method such as concentration under reduced pressure, and so on.

The propargylamine compound can also be taken out as its acid salt by recrystallization from the aqueous phase after separation.

In case of recrystallizing, the aqueous phase may be used as it is, but it is preferred that the aqueous phase is previously concentrated in view of the yield. In order to concentrate the aqueous phase, the aqueous phase may be heated under normal or reduced pressure, or azeotropic dehydration may be conducted by heating after adding an organic solvent capable of azeotropically distilling with water to the aqueous phase.

Examples of the organic solvent used for azeotropic dehydration include aromatic hydrocarbon such as benzene, toluene, xylene, and the like; aliphatic hydrocarbon such as hexane, cyclohexane, heptane and the like; halogenated hydrocarbon such as chlorobenzene, dichlorobenzene and the like; ketones such as methyl ethyl ketone, methyl isobutyl ketone and the like; alcohols such as ethanol, 2-propanol and the like; and ethers such as diisopropyl ether and the like. These solvent may be used alone or in combination thereof. An amount of the organic solvent used is normally within the range from 0.1 to 20 parts by weight, preferably from 0.2 to 10 parts by weight, to 1 part by weight of the aqueous phase.

The concentration due to azeotropic dehydration can be conducted under normal pressure, but in view of the stability of the propargylamine compound, it is preferably conducted under reduced pressure so that azeotropic dehydration can be conducted at not more than 85° C., more preferably from 35° to 85° C.

In case of azeotropic dehydration, the concentration can also be continuously conducted without supplementing more organic solvent by circulating the organic phase obtained by separating the distilled azeotropic mixture to the concentrating aqueous phase. For example, a Dean-Stark trap can be used for separation.

An amount of water of the mixture after concentration is preferably not more than 3 parts by weight, more preferably from 0.2 to 1.5 parts by weight, to 1 part by weight of the propargylamine compound.

Then, the propargylamine compound can be isolated as a salt thereof by adding a poor solvent, cooling and filtering the precipitated crystal.

Examples of the poor solvent include alcohols such as methanol, ethanol, 2-propanol and the like; ethers such as ethylene glycol dimethyl ether and the like; and nitriles such as acetonitrile and the like. These poor solvents may be used alone or in combination thereof. An amount of the poor solvent used is normally within the range from 0.5 to 20 parts by weight, preferably from 1.5 to 10 parts by weight, to 1 part by weight of water in the aqueous phase. The temperature of the following cooling is normally within the range from −5° to 30° C., preferably from 0° to 15° C.

Thus, the propargylamine compound forms a salt with the acid used in the above-mentioned hydrolysis and deposits as a crystal of the acid salt thereof. This crystal can be easily separated by a normal method such as filtration, and so on.

When using a hydrophilic organic solvent in the above-mentioned hydrolysis, the propargylamine compound can be obtained as the acid salt thereof, for example, by adding the poor solvent to the reaction mixture after hydrolysing. Examples of the poor solvent include alcohols such as methanol, ethanol, 2-propanol and the like.

Examples of the propargylamine compound thus obtained include propargylamine, 2-butynylamine, 2-pentynylamine, 4-methyl-2-pentynylamine, 2-hexynylamine, 4-methyl-2-hexynylamine, 5-methyl-2-hexynylamine, 2-heptynylamine, 5-methyl-2-heptynylamine, 2-octynylamine, 2-nonylamine, 3-phenyl-2-propynylamine, 3-(4-fluorophenyl)-2-propynylamine, 3-(3-chlorophenyl)-2-propynylamine, 3-(2-bromophenyl)-2-propynylamine, 3-(4-nitrophenyl)-2-propynylamine, 3-(4-methylphenyl)-2-propynylamine, 3-(4-methoxyphenyl)-2-propynylamine, 3-(2,4-dimethylphenyl)-2-propynylamine, 3-(2,4,5-trimethylphenyl)-2-propynylamine, 3-(1-naphthyl)-2-propynylamine, 3-(2-naphthyl)-2-propynylamine, 3-(2-thienyl)-2-propynylamine, 3-(5-fluoro-2-thienyl)-2-propynylamine, 3-(5-chloro-2-thienyl)-2-propynylamine, 3-(5-bromo-2-thienyl)-2-propynylamine, 3-(5-methyl-2-thienyl)-2-propynylamine, 3-(3-thienyl)-2-propynylamine, 3-(5-fluoro-3-thienyl)-2-propynylamine, 3-(5-chloro-3-thienyl)-2-propynylamine, 3-(5-bromo-3-thienyl)-2-propynylamine, 3-(5-methyl-3-thienyl)-2-propynylamine, 3-(2-furyl)-2-propynylamine, 3-(5-fluoro-2-furyl)-2-propynylamine, 3-(5-chloro-2-furyl)-2-propynylamine, 3-(5-bromo-2-furyl)-2-propynylamine, 3-(5-methyl-2-furyl)-2-propynylamine, 3-(3-furyl)-2-propynylamine, 3-(5-fluoro-3-furyl)-2-propynylamine, 3-(5-chloro-3-furyl)-2-propynylamine, 3-(5-bromo-3-furyl)-2-propynylamine, 3-(5-methyl-3-furyl)-2-propynylamine and the like.

Examples of the acid salt of the propargylamine compound include hydrochloride, sulfate, hydrobromide, p-toluenesulfonate, benzenesulfonate, methanesulfonate and the like of the above respective compounds.

Although the desired propargylamine compound and aromatic aldehyde represented by the general formula (III) are simultaneously produced by the hydrolysis, the aromatic aldehyde is included in the organic phase after partitioning and can be easily recovered from the organic phase by a ordinary method such as distillation and the like. The aromatic aldehyde thus recovered can be reused for the method of the present invention.

According to the method of the present invention, the propargylamine compound can be produced by a simple operation without using a special facility, without producing a dipropargylamine compound and a tripropargylamine compound as by-products.

The following Examples further illustrate the present invention in detail but are not to be construed to limit the scope thereof.

Example 1

Propargyl methanesulfonate (46.8 g, 0.35 mol) and benzaldehyde (47.0 g, 0.44 mol) were dissolved in 148 g of toluene and an aqueous 28% ammonia solution (180 g, 2.96 mol) was added dropwise at 24° C. over 7.5 hours to the solution, followed by stirring at the same temperature for 15 hours. After separating, the resultant organic phase was washed with water and concentrated to obtain 56.5 g of a crude product containing 40.0 g (yield: 80%) of N-benzylidene-2-propynylamine. The resulting crude product was distilled to obtain 34.9 g (purity: 97%, boiling point: 80°–83° C./2.5 mmHg) of N-benzylidene-2-propylamine.

To the resulting N-benzylidene-2-propylamine (24.8 g, 0.17 mol), 24.8 g of toluene was added. And 36% hydrochloric acid (20.7 g, 0.2 mol) was added dropwise at 60° C. over one hour, followed by stirring at 60° C. for 1.5 hours. Then, 3.5 g of water was added and the mixed solution was separated to obtain the aqueous phase and organic phase. The organic phase was extracted once with 5 g of water and the resulting aqueous phase was combined with the above aqueous phase. To the mixture, 64 g of 2-propanol was added at 60° C. and after cooling to 5° C., the deposited crystal was obtained by filtration. This crystal was washed with 20 g of 2-propanol three times and dried to obtain propargylamine hydrochloride (10.1 g, purity: 100%, yield: 65%).

On the other hand, the organic phase (41.7 g) after separating was quantitatively analyzed by a gas chromatography (internal standard). As a result, benzaldehyde (18.4 g, 0.17 mol) was contained.

Example 2

Propargyl methanesulfonate (31.6 g, 0.236 mol) and benzaldehyde (31.9 g, 0.3 mol) were dissolved in 103 g of toluene and an aqueous 28% ammonia solution (122 g, 2 mol) was added dropwise at 21° C. over 8 hours to the solution, followed by stirring at the same temperature for 15 hours. After separating, the resultant organic phase was washed with water and concentrated until the weight became 57.3 g to obtain a toluene solution containing 28.6 g (yield: 85%) of N-benzylidene-2-propynylamine.

To the resulting solution, 36% hydrochloric acid (30.4 g, 0.3 mol) was added dropwise at 20° C. over one hour, followed by stirring at 20° C. for 2 hours. Then, 2.5 g of water was added and the mixed solution was separated at 60° C. to obtain the aqueous phase and organic phase. The organic phase was extracted once with 5 g of water and the resulting aqueous phase was combined with the above aqueous phase. After 42.4 g of toluene was added, the mixture was heated to 62° C. and dehydrated by azeotropic distillation under 120 mmHg. Thus 10.6 g of water was distilled off. After returning to an atmospheric pressure, 18.8 g of 2-propanol was added to the mixture at 60° C. After cooling, the deposited crystal was obtained by filtration. This crystal was washed twice with 15 g of 2-propanol and dried to obtain propargylamine hydrochloride (18.1 g, purity: 86%, yield: 85%).

Example 3

An aqueous 28% ammonia solution (166.4 g, 2.74 mol) and benzaldehyde (30.6 g, 0.288 mol) were mixed and a solution prepared by dissolving propargyl methanesulfonate (36.7 g, 0.274 mol) in 147 g of toluene was added dropwise at 20°–25° C. over 3 hours to the solution, followed by stirring at the same temperature for 3 hours. After separating, the organic phase and aqueous phase were obtained. The organic phase obtained by washing the aqueous phase twice with 25 g of toluene was combined with the above organic phase and concentrated until the weight became 78 g to obtain a toluene solution of N-benzylidene-2-propynylamine.

To this solution, 36% hydrochloric acid (41.7 g, 0.411 mol) was added dropwise at 20°–25° C. over 10 minutes, followed by stirring at 20°–25° C. for 2.5 hours. Fifty grams of ethanol was added and, after cooling to 5° C., the deposited crystal was obtained by filtration and the filtrate was simultaneously obtained. This crystal was washed once with 25 g of ethanol and dried to obtain 13.7 g of propargylamine hydrochloride.

The filtrate and wash ethanol after the crystal was obtained by filtration were combined and, after separating, the resulting lower layer was concentrated until the weight became 82 g. After cooling to 5° C., the deposited crystal was obtained by filtration. This crystal was washed once with 6.2 g of ethanol and dried to obtain 3.2 g of propargylamine hydrochloride.

This propargylamine hydrochloride and the propargylamine hydrochloride obtained above were combined (weight: 16.9 g). As a result, the purity was 94% and the yield to the raw material (propargyl methanesulfonate) was 63%.

Example 4

An aqueous 28% ammonia solution (12.1 g, 200 mmol) and o-chlorobenzaldehyde (3.65 g, 26 mmol) were mixed and a solution prepared by dissolving propargyl methanesulfonate (2.68 g, 20 mmol) in 10.7 g of toluene was added dropwise at 20° C. over 0.6 hour to the solution, followed by stirring at the same temperature for 10 hours. After separating, the resulting organic phase was concentrated to obtain a crude product of N-(2-chlorobenzylidene)-2-propynylamine.

To this crude product, 5 ml of ethanol and 36% hydrochloric acid (3.0 g, 30 mmol) were added, followed by stirring at 20° C. for 5 hours. After cooling to 5° C., the deposited crystal was obtained by filtration and the filtrate was simultaneously obtained. The obtained crystal was washed with ethanol and dried to obtain 878 mg of propargylamine hydrochloride. The filtrate was concentrated and recrystallized from ethanol to obtain 546 mg of propargylamine hydrochloride. These propargylamine hydrochlorides were combined (weight: 1.42 g). As a result, the purity was 99% and the yield to the raw material (propargyl methanesulfonate) was 78%.

Example 5

According to the same manner as that described in Example 4 except for using p-methoxybenzaldehyde (3.54 g, 26 mmol) in place of o-chlorobenzaldehyde, the operation was conducted to obtain propargylamine hydrochloride (1.32 g, purity: 87%, yield: 63%).

Example 6

According to the same manner as that described in Example 4 except for using benzaldehyde (2.76 g, 26 mmol) in place of o-chlorobenzaldehyde, propargyl benzenesulfonate (3.92 g, 20 mmol) in place of propargyl methanesulfonate and 19.6 g of toluene in place of 10.7 g of toluene, the operation was conducted to obtain propargylamine hydrochloride (1.40 g, purity: 99%, yield: 77%).

Example 7

An aqueous 28% ammonia solution (12.1 g, 200 mmol) and benzaldehyde (2.23 g, 21 mmol) were mixed and a solution prepared by dissolving propargyl bromide (2.38 g, 20 mmol) in 9.5 g of toluene was added dropwise at 20° C. over 0.7 hour to the solution, followed by stirring at the same temperature for 10 hours. After separating, the resulting organic phase was concentrated until the weight became to 10 g to obtain a toluene solution containing N-benzylidene-2-propynylamine.

To this solution, 36% hydrochloric acid (3.0 g, 30 mmol) was added, followed by stirring at 20° C. for 5 hours. Then, the toluene phase was removed by decantation. After cooling to 5° C., the deposited crystal was obtained by filtration and the filtrate was simultaneously obtained. The resulting crystal was washed with ethanol and dried to obtain 889 mg of propargylamine hydrochloride. The filtrate was concentrated and recrystallized from ethanol to obtain 271 mg of propargylamine hydrochloride. The resulting propargylamine hydrochlorides were combined (weight: 1.16 g). As a result, the purity was 99% and the yield to the raw material (propargyl methanesulfonate) was 63%.

Example 8

According to the same manner as that described in Example 7 except for using propargyl chloride (1.49 g, 20 mmol) in place of propargyl bromide and 6.0 g of toluene in place of 9.5 g of toluene, the operation was conducted to obtain propargylamine hydrochloride (790 mg, purity: 96%, yield: 42%).

Example 9

2-Butynyl methanesulfonate (18.7 g, 126 mol) and benzaldehyde (17.8 g, 168 mmol) were dissolved in 64 g of toluene and an aqueous 28% ammonia solution (68.1 g, 1.12 mol) was added dropwise at 23° C. over 3.5 hours to the solution, followed by stirring at the same temperature for 6 hours. After separating, the resulting organic phase was washed with water and concentrated to obtain 24.3 g of a crude product containing 17.4 g (yield: 88%) of N-benzylidene-2-butynylamine. To obtain 10.6 g (purity: 98%) of N-benzylidene-2-butynylamine, 17.3 g of this crude product was distilled off.

Boiling point: 83°–85° C./0.4 mmHg $^1$H-NMR (270 MHz, CDCl$_3$): δ 1.92 (t, 3H, J=2.3Hz), 4.4–4.5 (m, 2H), 7.4–7.5 (m, 3H), 7.7–7.8 (m, 2H), 8.56 (s, 1H)

To the resulting N-benzylidene-2-butynylamine (9.56 g, 60 mmol), 19.1 g of toluene and 1 g of water were added and 36% hydrochloric acid (20.7 g, 0.2 mol) was added dropwise at 60° C. over one hour, followed by stirring at 60° C. for 3 hours. Then, 2.5 g of water was added and the mixed solution was separated at 60° C. to obtain the aqueous phase and organic phase. The aqueous phase obtained by extracting organic phase (24.9 g) once with 4 g of water was combined with the above aqueous phase. To this aqueous phase (18.2 g) was added 18.2 g of toluene and, after the mixture was heated to 62° C. and dehydrated by azeotropic distillation under 90 mmHg, 10 g of water was distilled off. After returning to an atmospheric pressure, 10 g of 2-propanol was added to the mixture at 60° C. After cooling to 5° C., the deposited crystal was obtained by filtration. This crystal was washed twice with 5 g of 2-propanol and dried to obtain propargylamine hydrochloride (5.93 g, purity: 100%, yield: 94%).

On the other hand, the organic phase (24.9 g) obtained by separating was quantitatively analyzed by a gas chromatography (internal standard). As a result, benzaldehyde (6.15 g, 58 mol) was contained.

Example 10

3-Phenyl-2-propargyl methanesulfonate (29.2 g, 139 mmol) and benzaldehyde (17.8 g, 168 mmol) were dissolved in 88.5 g of toluene and an aqueous 28% ammonia solution (68.1 g, 1.12 mol) was added dropwise at 23° C. over 8 hours to the solution, followed by stirring at the same temperature for 20 hours. After separating, the resultant organic phase was washed with water and concentrated to obtain 39.5 g of a crude product containing 17.2 g (yield: 57%) of N-benzylidene-3-phenyl-2-propynylamine. In the crude product 12.7 g of unreacted 3-phenyl-2-propynyl methanesulfonate was contained.

To 21.7 g of this crude product, 21.7 g of toluene and 2 g of water were added and 36% hydrochloric acid (12.2 g, 120 mol) was added dropwise at 60° C. over one hour, followed by stirring at 60° C. for 3 hours. Then, 9 g of water was added and the mixed solution was separated to obtain the aqueous phase and organic phase. The organic phase was extracted once with 5 g of water and the resulting aqueous phase was combined with the above aqueous phase, followed by washing once with 20 g of toluene at 50° C. To this aqueous phase, 70 g of toluene was added and an aqueous 27% sodium hydroxide solution (22.2 g, 150 mmol) was added dropwise at 40°–50° C. over one hour, followed by stirring at 40° C. for 0.5 hour. After the reaction mixture was separated at room temperature, the organic phase was washed with 20 g of an aqueous saturated sodium chloride solution, concentrated and dried to obtain 3-phenyl-2-propynylamine (4.54 g, purity: 97%, yield: 78%).

Example 11

3-(2-Thienyl)-2-propynyl methanesulfonate (2.47 g, 11.4 mmol) and benzaldehyde (1.51 g, 14.3 mmol) were dissolved in 15.9 g of toluene and an aqueous 28% ammonia solution (5.89 g, 97 mol) was added dropwise at 23° C. over one hour to the solution, followed by stirring at the same temperature for 22 hours. After separating, the resultant organic phase was washed with water and concentrated to obtain 18.7 g of a toluene solution containing 1.49 g (yield: 60%) of N-benzylidene-3-(2-thienyl)-2-propynylamine.

To 17.7 g of this toluene solution, 36% hydrochloric acid (1.27 g, 12.5 mol) was added dropwise at 60° C. over 10 minutes, followed by stirring at 60° C. for 1.5 hours. Then, 4 g of water was added and the mixed solution was separated to obtain the aqueous phase and organic phase. The organic phase was extracted once with 2.5 g of water and the resulting aqueous phase was combined with the above aqueous phase. To this aqueous phase, 15 g of toluene was added and an aqueous 27% sodium hydroxide solution was added dropwise at 23° C. over 15 minutes, followed by stirring at 23° C. for 0.5 hours. After separating at the same temperature, the resulting organic phase was washed with 5 g of an aqueous saturated sodium chloride solution, concentrated and dried to obtain 3-(2-thienyl)-2-propynylamine (0.73 g, purity: 87%, yield: 77%).

Reference 1

To an aqueous 28% ammonia solution, propargyl methanesulfonate (0.90 g, 6.7 mmol) was added dropwise at 20° C. over 3.5 hours. Then, the reaction mixture was analyzed by gas chromatography. As a result, a formation ratio of propargylamine, dipropargylamine and tripropargylamine was 29:48:20.

What is claimed is:

1. A method for producing a propargylamine compound represented by the general formula (I):

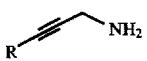 (I)

which comprises reacting a propargyl compound represented by the general formula (II):

 (II)

with an aromatic aldehyde represented by the general formula (III):

ArCHO (III)

and ammonia to obtain an imine compound represented by the general formula (IV):

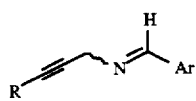 (IV)

and hydrolyzing the resultant imine compound.

2. A method for producing an imine compound represented by the general formula (IV), which comprises reacting a propargyl compound represented by the general formula (II) with an aromatic aldehyde represented by the general formula (III) and ammonia.

3. The method according to claim 1 or 2, wherein an amount of the aromatic aldehyde used is from 0.5 to 10 mol to 1 mol of the propargyl compound.

4. The method according to claim 1 or 2, wherein an amount of ammonia used is from 2 to 20 mol to 1 mol of the propargyl compound.

5. The method according to claim 1 or 2, wherein an aqueous ammonia solution is used as ammonia.

6. The method according to claim 5, wherein a concentration of the aqueous ammonia solution is from 5 to 30% by weight.

7. The method according to claim 1, wherein the hydrolysis is conducted using an acid.

8. The method according to claim 7, wherein an amount of the acid used is from 0.45 to 5 mol to 1 mol of the imine compound.

* * * * *

UNITED STATES PATENT AND TRADEMARK OFFICE
CERTIFICATE OF CORRECTION

PATENT NO. : 5,756,769
DATED : May 26, 1998
INVENTOR(S) : Shinzo Seko et al.

It is certified that error appears in the above-identified patent and that said Letters Patent is hereby corrected as shown below:

Claim 1,
Line 7, immediately following formula (I) and before "which comprises", please insert the following: -- wherein R represents hydrogen, a lower alkyl group, an aryl group or a heteroaryl group, --.
Line 12, immediately following formula (II) and before "with an", please insert the following: -- wherein R has the same meaning as defined above; and X represents a halogen atom or a sulfonyloxy group --.
Line 12, please change "with an aromatic" to -- with ammonia and an aromatic --.
Line 16, immediately following formula (III) and before "and ammonia", please insert the following: -- wherein Ar represents an aryl group --.
Line 23, immediately following formula (IV) and before "and hydrolyzing", please insert the following: -- wherein R and Ar have the same meanings as defined above, --.

Signed and Sealed this

Sixteenth Day of April, 2002

*Attest:*

JAMES E. ROGAN
*Attesting Officer*     *Director of the United States Patent and Trademark Office*